(12) United States Patent
Makins

(10) Patent No.: US 9,750,225 B1
(45) Date of Patent: Sep. 5, 2017

(54) PET LITTER BOX

(71) Applicant: Brandon Makins, Etobicoke (CA)

(72) Inventor: Brandon Makins, Etobicoke (CA)

( * ) Notice: Subject to any disclaimer, the term of this patent is extended or adjusted under 35 U.S.C. 154(b) by 0 days.

(21) Appl. No.: 15/217,615

(22) Filed: Jul. 22, 2016

(51) Int. Cl.
*A01K 1/01* (2006.01)
*A01K 1/015* (2006.01)
*A01K 1/00* (2006.01)
*A61L 2/00* (2006.01)

(52) U.S. Cl.
CPC .......... *A01K 1/0114* (2013.01); *A01K 1/0047* (2013.01); *A01K 1/0157* (2013.01); *A61L 2/0047* (2013.01); *A61L 2/0052* (2013.01); *A61L 2202/11* (2013.01)

(58) Field of Classification Search
CPC ..... A01K 1/0107; A01K 1/011; A01K 1/0114
USPC .................. 119/167, 170, 165, 161
See application file for complete search history.

(56) References Cited

U.S. PATENT DOCUMENTS

| 3,831,557 A * | 8/1974 | Elesh | A01K 1/0107 119/170 |
| 4,352,340 A * | 10/1982 | Strubelt | A01K 1/0107 119/170 |
| 4,836,141 A * | 6/1989 | Whitfield | A01K 1/0107 119/169 |
| 5,183,009 A * | 2/1993 | Vito | A01K 1/0107 119/165 |
| 5,390,628 A * | 2/1995 | Vito | A01K 1/0107 119/165 |
| 5,794,566 A * | 8/1998 | Goetz | A01K 1/0107 119/161 |
| 6,223,688 B1 * | 5/2001 | Engel | A01K 1/0107 119/165 |
| 6,848,394 B1 * | 2/2005 | Sexton | A01K 1/011 119/165 |
| 7,610,877 B2 * | 11/2009 | Garfield | A01K 1/0107 119/170 |
| 8,438,994 B2 * | 5/2013 | Stratton | A01K 1/0107 119/161 |

* cited by examiner

*Primary Examiner* — Yvonne Abbott-Lewis
(74) *Attorney, Agent, or Firm* — Nasser Ashgriz; Uipatent Inc.

(57) ABSTRACT

The present invention is a cylindrical litter box with a litter pan and a lid, which is removably attached to the litter pan. The litter pan comprises of a body having a circular base, a cylindrical side wall that is joint at its bottom end to the circular base. The cylindrical pan includes an open top that is defined by a peripheral lip. The open top end includes a double brim: an outer brim dedicated to securely support the lid, an inner brim to support a clutch and secure a bag, and a cavity separating the two brims. An especially designed bag that can be rolled open is attached from its open end to the inner brim and lines the pan. The rolled part of the bag is secured inside the cavity in between the inner and outer brims.

19 Claims, 17 Drawing Sheets

FIG. 6A
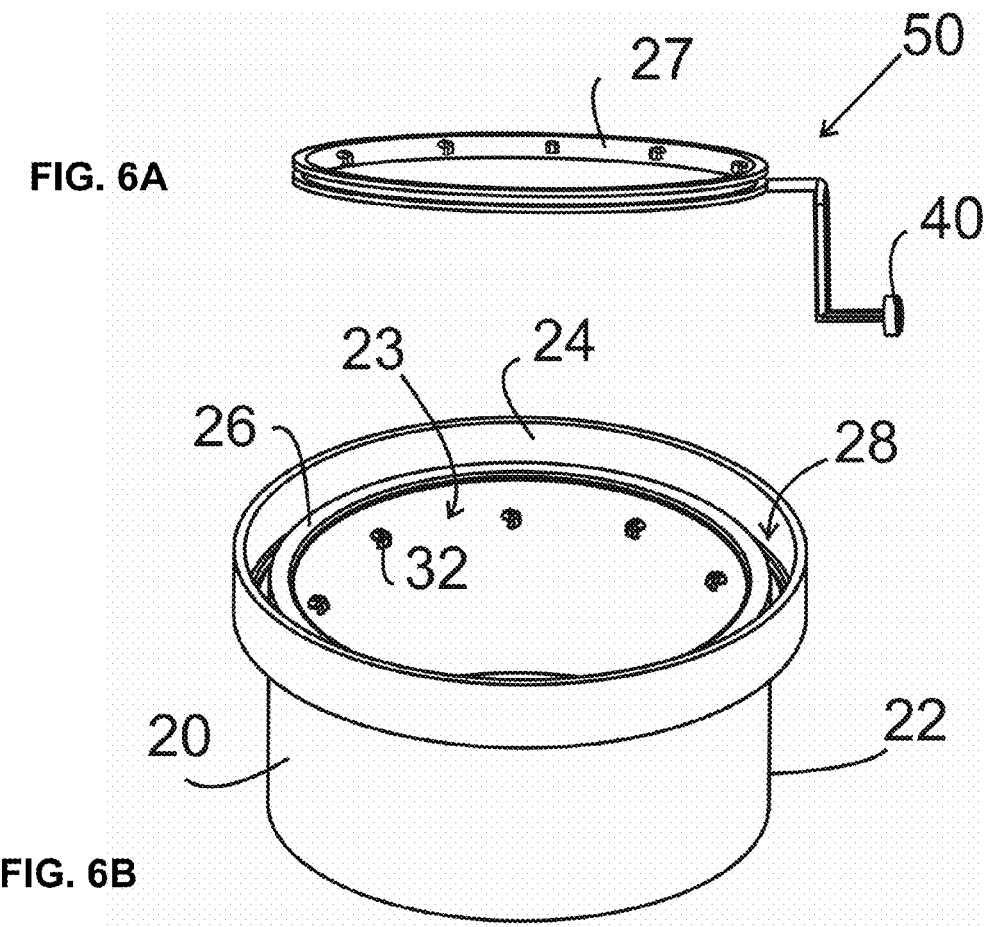
FIG. 6B
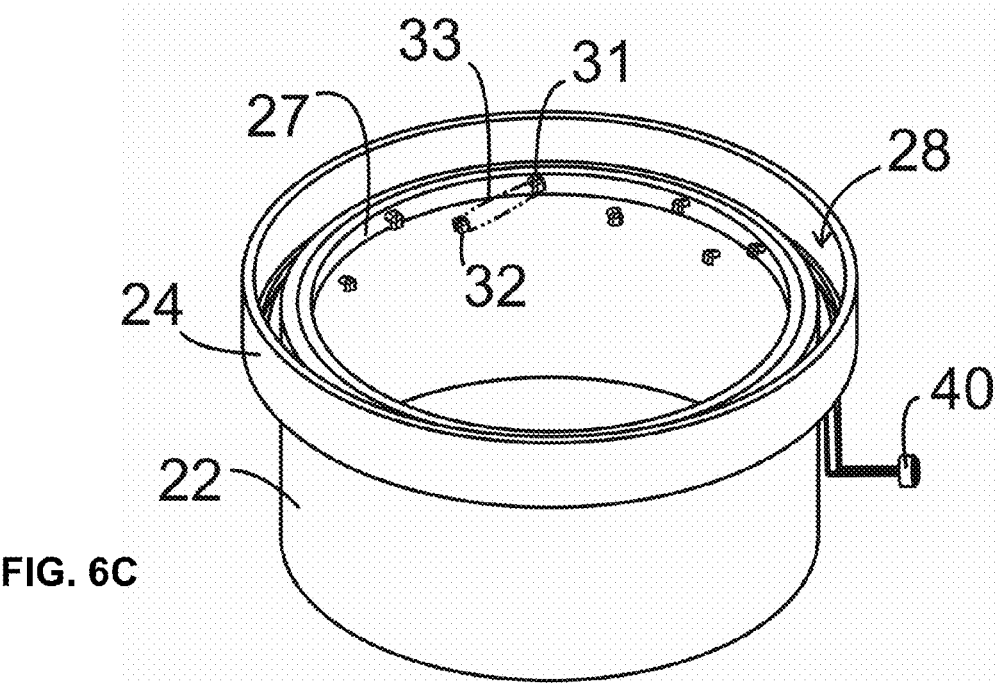
FIG. 6C

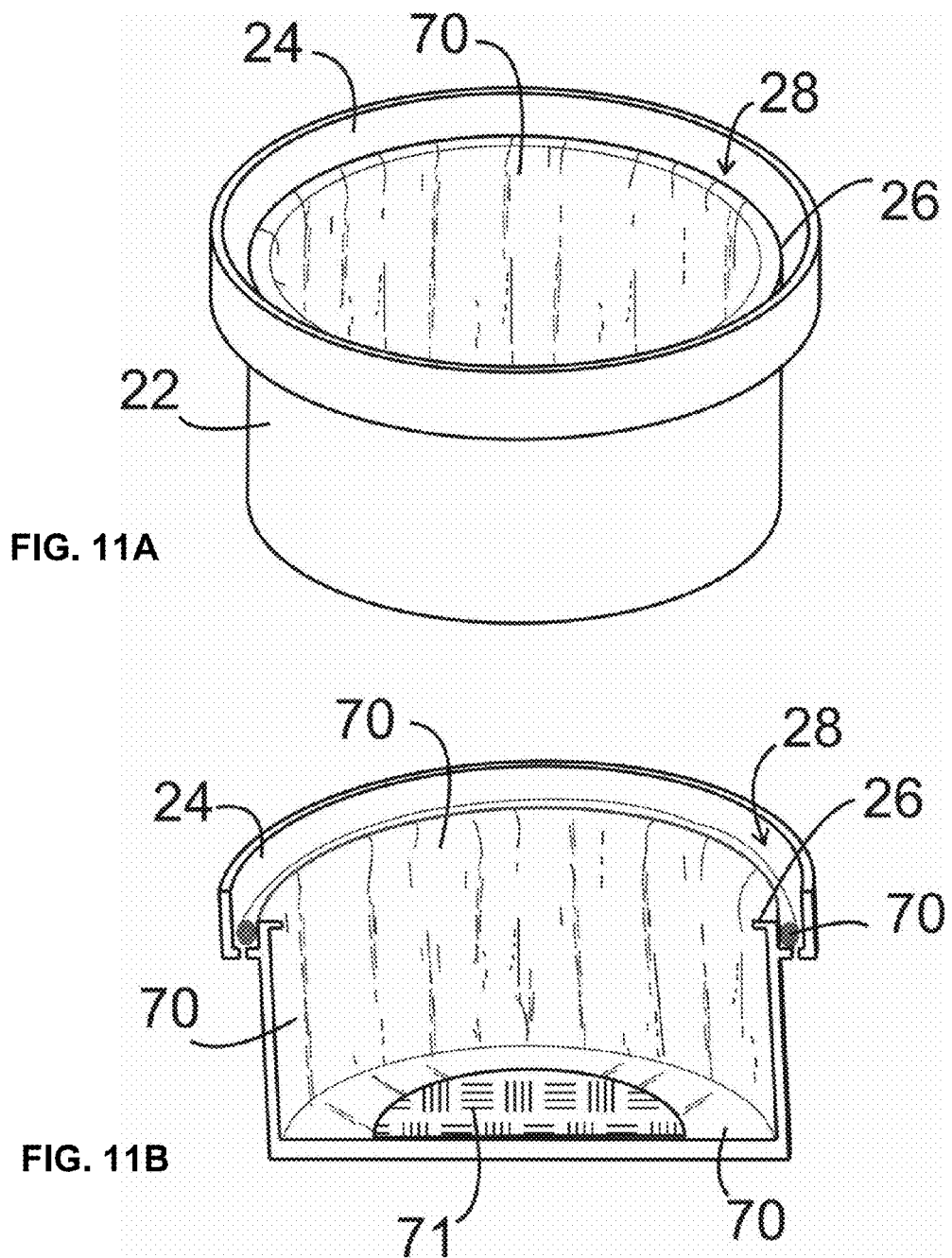

PET LITTER BOX

FIELD OF THE INVENTION

The present invention relates to a litter box, and more particularly, to a system for storing and collecting pet waste in a clean manner.

BACKGROUND OF THE INVENTION

Household cats are trained to use a litter box. Typically, the waste must be discarded regularly to manage the foul and unhealthy bi-products resulting from housing a litter box. Different types of self-cleaning litter boxes for storing pet waste and methods for changing the litter bags in litter boxes are disclosed in the prior arts.

The present invention intends to hide the unsightly litter that the prior art leave visible by use of a lid with a door. The present litter box is capable of managing the escape of odour, dust, debris, bacteria and noxious inhalants while functioning as a waste receptacle and it retains these benefits during litter changes. It provides a simple, fast and effective method for manually closing a bag and sifting the litter beneath the lid without requiring the operator to look at litter or come into contact with offensive and unhealthy bi-products.

SUMMARY OF THE INVENTION

The present invention is a cylindrical litter box comprising of a litter pan and a removable lid. The litter pan comprises of a body having a circular base, a cylindrical side wall that is joint at its bottom end to the circular base. The cylindrical pan includes a receptacle hollowed into its base to receive a retractable and removable tray that supports a litter mat. The cylindrical pan further includes an open top that is defined by a peripheral lip. The open top end includes a double brim: an outer brim dedicated to support the lid, an inner brim to support a clutch and secure a bag, and a cavity separating the two brims. An especially designed bag that can be lengthened by unrolling is attached from its rolled, open end to the inner brim. The rolled part of the bag is secured inside the cavity in between the inner and outer brims. This design enables proper operation of the clutch, prevents access to the bag by pets who like to chew on bags and ensures a tidy appearance.

A main litter bag clutch is mounted on the top end of the litter pan. The main clutch is incorporated as a part of the inner brim of the pan. The inner brim can either be the top vertical portion of the pan sidewall, thereby necessitating a fairing on the external aspect of the sidewall to create the outer brim that supports the lid and builds a cavity between the inner brim and outer brim or the outer brim can be the top vertical portion of the sidewall, thereby necessitating an internal fairing of the sidewall to create the inner brim that supports the clutch and builds a cavity between the inner and outer brims.

The main clutch of the present invention is used in conjunction with a litter box which is a shallow, wide pan. The litter pan formation was necessitated by the need for the litter box to be functional for an animal to enter it and move easily within it. In the preferred embodiment, the litter pan is 4.5 inches high, with an opening of 24 inches in diameter or any such measurements deemed appropriately accessible to a pet and achieve the benefits of this invention. The main clutch design was necessitated by the need for it to function, given the parameters of the pan.

The clutch is a mechanistic system comprised of an outer moveable ring with downward facing hooks and a control arm with handle, which envelopes the inner stationary ring attached to the inner brim of the pan and is connected by elastic bands to the pan mounted downward facing hooks.

The open top end of the litter pan includes two concentric rings that are imposed to one another, the internal stationary ring being the top of the pan's inner brim, is shaped like an inverted L with the flange bent at 90 degrees toward the centre. The external ring, being shaped like a boxed C, engulfs the flange and is movable on this track and whose top portion extends over the inner brim. The combination of these two components forms the double ring of the main clutch. On the backside or lower side of the C ring, there is a plurality of downward facing hooks mounted in a pre-defined distance apart.

The upper portion of the pan's internal wall has a plurality of corresponding downward facing hooks tucked somewhat beneath the clutch rings and set some distance behind their corresponding upper hooks; that is the upper hook supports the leading end of an elastic band attached to it and rotates around the circumference of the brim clockwise and away from its stationary corresponding hook.

A handle is attached to the movable ring and is in fact an extension of the upper portion of the C ring. The handle extends slightly beyond the inner brim into the cavity before bending downward at 90 degrees and running close and parallel to the outside of the inner brim. It is then bent 90 degrees and continues parallel to the floor above the base of the cavity until it exits the cavity via a narrow slit; this slit runs 180 degrees around the pan wall allowing the arm to traverse this same path. The arm terminates into a proper handle at the exterior of the pan for gripping.

When the handle is turned clockwise, the movable ring, its hooks and the ends of the elastic bands attached to those hooks rotate away from their corresponding stationary hooks, until finally coming to rest opposite of their starting point. These outstretched bands become twisted above the centre of the pan, thereby twisting any bag set in the pan prior to activating the clutch.

The litter bags are customized for the present litter box. They can be made of any flexible material, but preferably made of biodegradable material. The bags have perforations at their base to allow sifting. The perforations are covered by a reusable seal, which is removed before sifting and put back on after the completion of sifting. During manufacturing, the length of the bag is either rolled like a condom, or folded like an accordion, preferably rolled. A specific length, preferably 5 inches, is retained to line the interior of the pan and wrap over the inner brim. The dimensions of the bag are selected based on the size of the litter box, but they are preferably 24 inches in diameter and 24 inches long. The excess material shall serve as slack to be unrolled when the main clutch is engaged, pulling the bag's edge toward the centre and twisting it. The cavity in between the two brims is provided to store the rolled/corrugated portion of bag, giving the material somewhere to go, while ensuring proper operation of the clutch and keeping the product aesthetically pleasing and safe for pets.

A litter box lid is sized to be received on the litter pan. The lid comprises of a circular top connected to a cylindrical side wall, which is open at the bottom portion. The lid top wall defines a generally planar or curved top surface that includes in one embodiment of this invention a storage bracket, filtration vent and a receptacle cavity in the middle to receive a window and a lid clutch. The lid has a door opening on its side wall. The opening is large enough to receive most large cats. The opening is preferably covered by an electrostatic door, though other options, such as a magnetic door, are possible.

The lid clutch is provided to hold the litter bag tight for sifting purposes. In one embodiment of this invention, two concentric rings, T and C rings, are rotatably engaged on each other. The T ring sits on the edges of the receptacle cavity. There are a plurality pairs of hooks installed on the sides of the T ring. On the back side of the C ring, there are plurality pairs of hooks that correspond to the hooks on the stationary T ring. A plurality of Kevlar swatches are attached to the hooks. The swatch material can be any appropriate material to achieve the task of suspending a heavy bag. When open, the Kevlar swatches fall into the space beneath the lid forming a U shape, as two corners are affixed to the stationary T ring and the other two are attached to the movable C ring. An upward pointing protrusion is affixed to the top side of the movable ring and fashioned into a handle. When the handle is turned clockwise, the upper ring moves taking with it one end of the Kevlar swatches. When the movable end of the swatches comes to a stop at 180 degrees opposite its starting point, the clutch is closed and the Kevlar swatches outstretched and intertwined such that they create a sealed barrier able to grab and secure the litter bag in an elevation from the litter pan base.

In another embodiment of the present invention the lid clutch is a mechanical iris, which is surrounded by internal ambient LED and UV-C LED disinfection system. For this reason, the lid interior is coated with a reflective material to enhance the effect of both the ambient and UV-C LEDs.

A removable litter mat is also provided inside a removable, retractable tray of the litter pan. The mat is sized to cover the area below the door outside of the litter pan to collect litter spatter and comb debris off of paws.

It is an object of the present invention to provide a device and system to hide unsightly litter and control the escape of unpleasant odors, debris, bacteria and noxious inhalants while as a waste container and during litter changes.

It is another object of the present invention to provide a customized disposable biodegradable bag that can be outstretched while being twisted closed and that can permit sifting of litter from waste or in another embodiment absorb liquid via a base pad.

It is another object of the present invention to provide a main clutch system to twist the litter bag close in the pan before removing the litter box lid.

It is another object of the present invention to provide a sifting system through using a lid litter bag clutch to support a used bag during the sifting process and along with the lid and door, to ensure odours, dust, debris, noxious inhalants and bacteria diffusion are contained beneath the lid.

It is another object of an embodiment of the present invention to provide a transparent lid window when closed to allow assessment of bin capacity.

It is another object of an embodiment of the present invention to provide a transparent iris on the lid as a window and a lid clutch to hold the bag during sifting.

It is another object of the present invention to provide a simple, fast and effective way to collect waste and either separate it from reusable litter or dispose of it entirely without the operator having to see or smell the litter or contend with foul bi-products or contaminated litter bags.

It is another object of the present invention to provide a litter box that is of environmentally conscious construction using natural and recyclable materials.

It is another object of the present invention to provide a roof vent to allow for fresh air circulation, while supporting the air filtration system.

It is another object of the present invention to provide an overlapping electrostatic or magnetic door through which the pet enters and leaves and that creates a tight seal to contain odours, dust, debris, noxious inhalants and germ diffusion.

Other objects, features, and advantages of the present invention will be readily appreciated from the following description. The description makes reference to the accompanying drawings, which are provided for illustration of the preferred embodiment. However, such embodiments do not represent the full scope of the invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which

FIG. 6A is a perspective view of the moveable ring of the clutch system according to the present invention;

FIG. 6B is a perspective view of the pan of the litter box;

FIG. 6C is a perspective view of the pan and the clutch mounted thereon;

FIG. 11A is a perspective view of the litter pan and the position of the litter bag in the pan;

FIG. 11B is a perspective view of the litter pan and the position of the litter bag in the pan;

DETAILED DESCRIPTION OF THE DRAWINGS

Figure 1A:
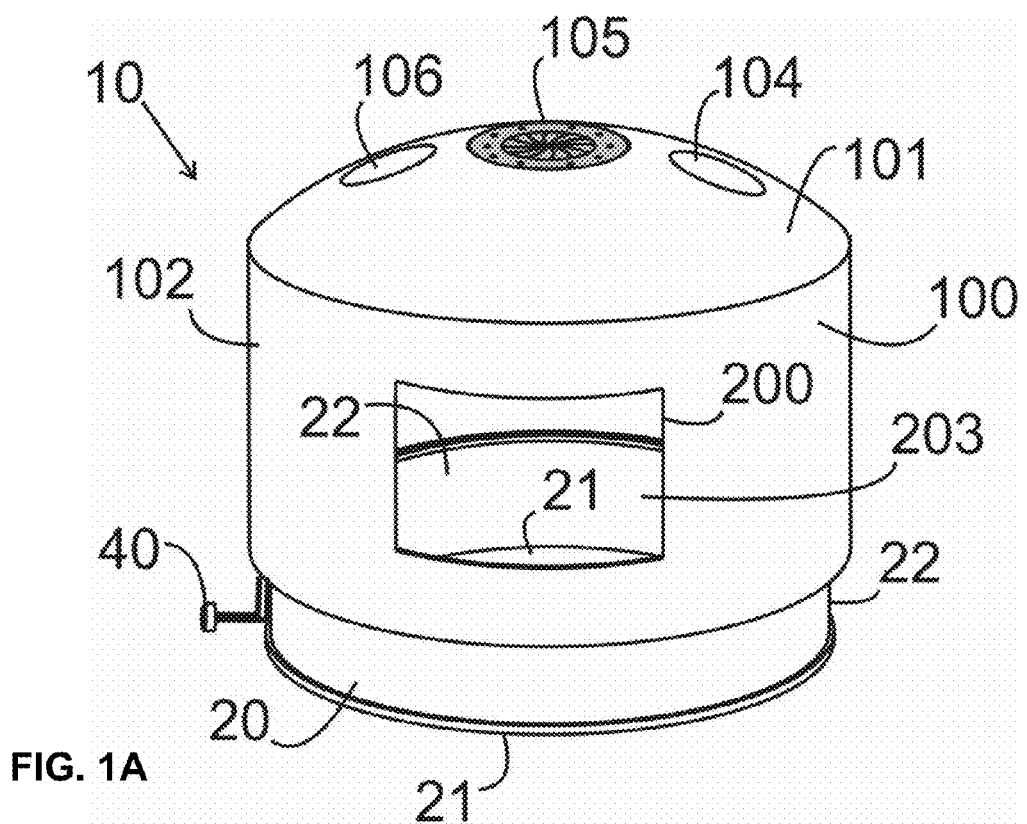
FIG. 1A is a perspective view of the pet litter box.
Figure 1B:
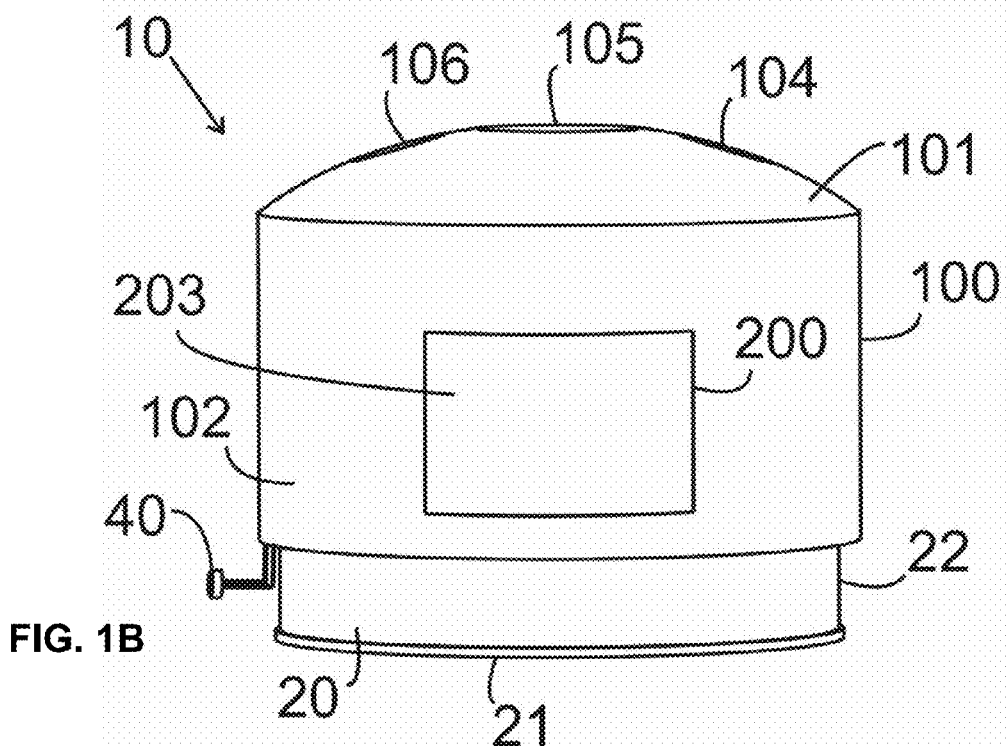
FIG. 1B is a perspective view of the pet litter box.

FIGS. 1A and 1B show the cylindrical pet litter box 10 comprising of a litter pan 20 and a lid 100, which is removably attached to the litter pan 20. The litter box 10 is preferably made of non-stick antimicrobial plastic pan with curved inner edges. The litter pan can have any size, but is preferably 4.5 inches high, and has an opening of 24 inches in diameter and accessible to a large pet. The litter pan 20 comprises of a body having a circular base 21, a cylindrical side wall 22 that is joined at its bottom end to the circular base 21.

The litter box lid 100 is sized to be received on the litter pan 20 and comprises of a top wall 101. In one embodiment of the present invention, the lid top wall 101 defines a generally planar or curved top surface that comprises of a receptacle cavity in the middle to receive a lid clutch 105 and a lid window. Said litter box lid 100 has a height, tall enough to fit a large pet. The lid 100 further comprises of a vent 104 and a clutch storage compartment 106.

The litter box 10 further comprises of a removable and overlapping electrostatic or magnetic door 200 mounted on the door opening 203 cut in the front part of the side wall 102 of the litter box lid 100 through which the pet enters and leaves the litter box 10.

Figure 2:
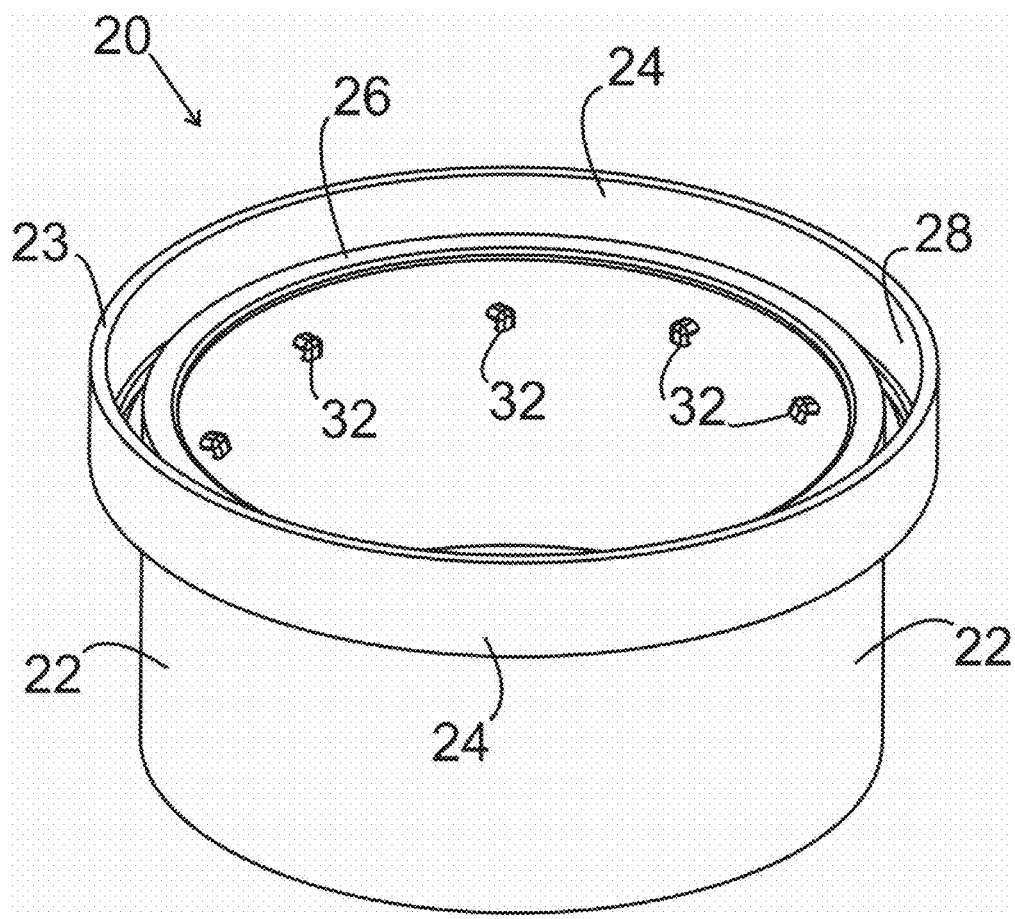
FIG. 2 is a perspective view of the litter pan.
Figure 3A:
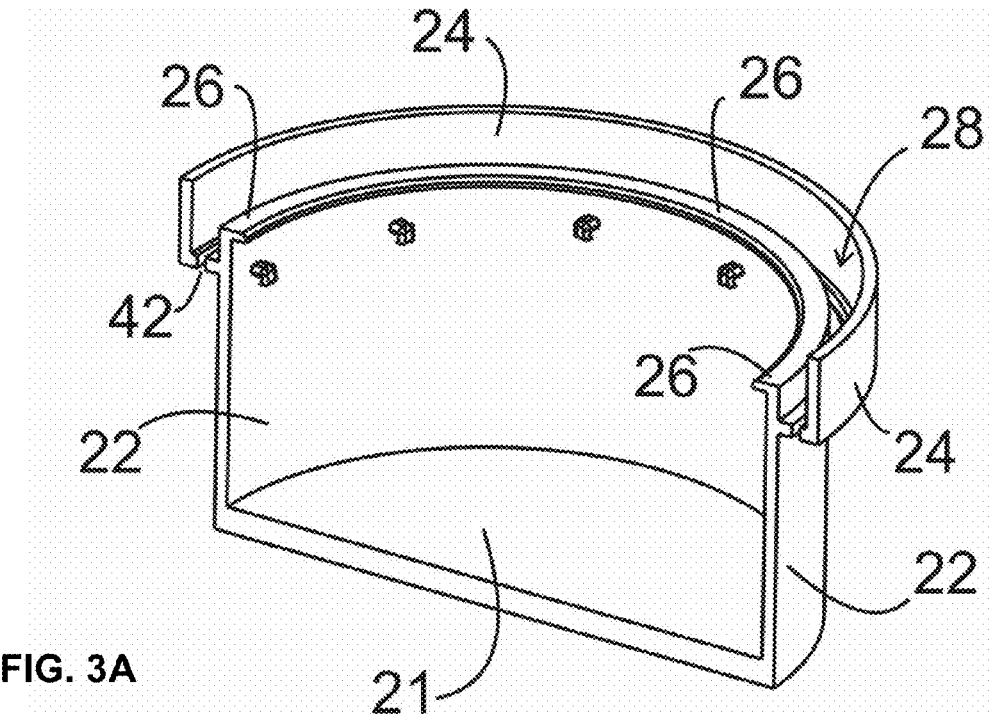
FIG. 3A is a perspective side view of the pan of the litter box, broken away, showing the interior of the pan.
Figure 3B:
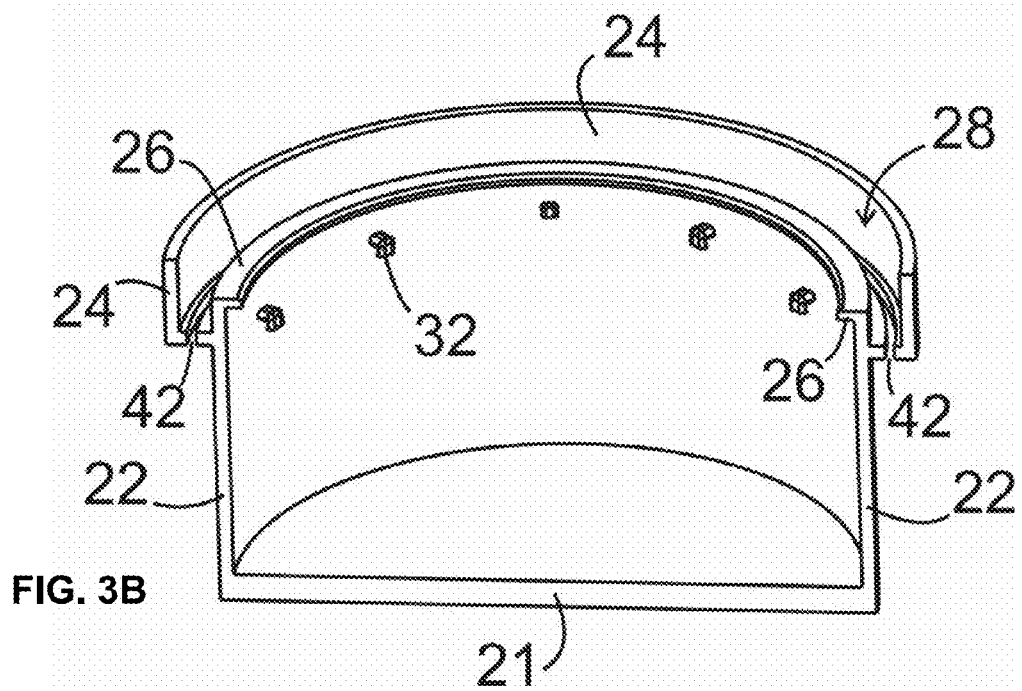
FIG. 3B is a perspective side view of the pan of the litter box, broken away, showing the interior of the pan.

According to FIGS. 2, 3A, and 3B, the top end of the pan 23 has a double brim: an outer brim 24 dedicated to support the lid and an inner brim 26, which is a part of the main clutch. A bag-space 28 is built between the inner brim 26 and outer brim 24 to receive a folded bag. A bag is folded and stored in the bag-space and a part of it is secured to the inner brim 26. The bag-space 28 creates a neat look, prevents access to the bag by pets who like to chew bags and ensures proper operation of the clutch.

Figure 4:
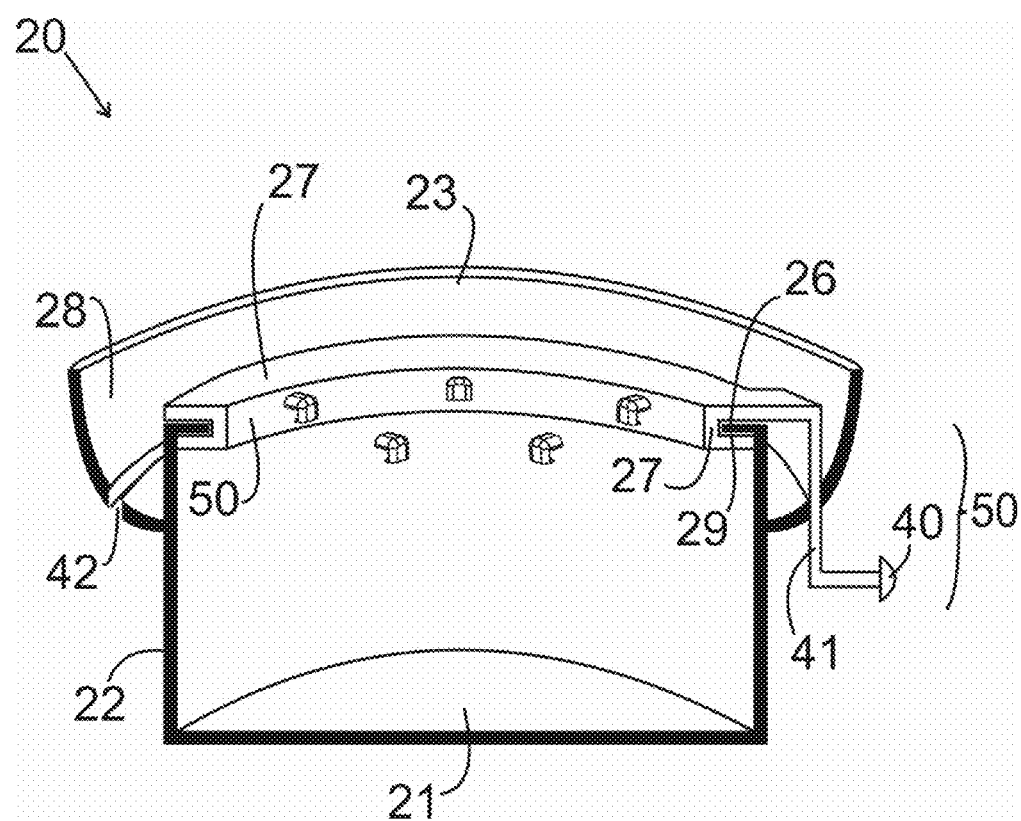
FIG. 4 is a perspective side view of the pan of the litter box, broken away, showing the interior of the pan and the clutch system.

FIG. 4 shows the clutch system 50 of the present invention to twist and close the litter bag in the litter box. The main clutch 50 is a part of the inner brim of the litter pan 20 and comprises of a circular ring 27, which engages with the inner brim 26 of the pan 20. The circular ring 27 has a C-shaped slot 29, which engages with the inner brim 26 and provides a circular movement for the clutch 50. The inner brim 26 is in a form of an inverted L-shaped ring 26, which engages with the C-shaped ring 27 of the clutch 50.

Figures 5A, 5B, 5C:
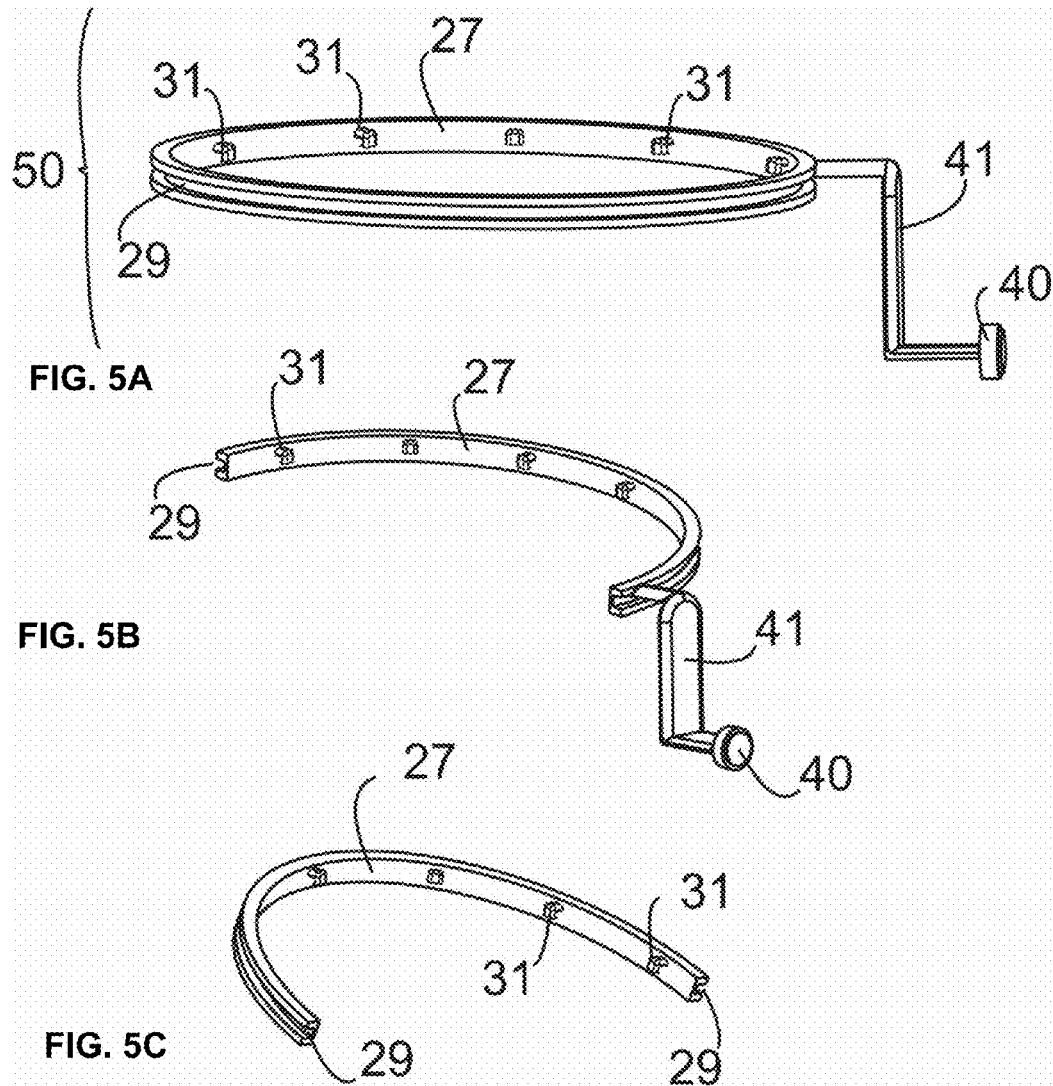
FIG. 5A is a perspective view of the moveable ring according to the present invention.
FIG. 5B is a perspective view of the moveable ring according to the present invention.
FIG. 5C is a perspective view of the moveable ring according to the present invention.

The main clutch 50 further comprises of a handle 40 having an arm 41, which is attached to the C-shaped ring 27. The handle 40 is an extension of the upper portion of the C-shaped ring 27. The handle 40 extends slightly beyond the inner brim 26 into the bag-space 28 before bending downwards at 90 degrees and further extending parallel to the side wall 22. The handle 40 extends out from the bag-space 28 through a slot 42 for moving the clutch 50 FIGS. 5A, 5B and 5C illustrate the C shape movable ring 27 of the main clutch 50. A plurality of hooks 31 are mounted on the inner side of the moveable ring.

The main clutch 50 is used in conjunction with a shallow and wide pan 20 of the present invention. The litter pan 20 is preferably 4.5 inches in height with an opening of 24 inches in diameter so as to be accessible to a pet. The clutch 50 traverses a the 24 inch opening of the litter pan 20 when engaged but retracts to less than the 4.5 inches of the pan side wall 22 when open.

According to FIGS. 6A, 6B and 6C, the main clutch system 50 is mounted on the open top end 23 of the litter pan 20 and is engaged with the inner brim 26 of the pan 20. The L-shaped inner brim 26 engages with the movable C-shaped ring 27 and in conjunction with the hooks 31, 32 and elastic bands 33 creates the main clutch system of the present invention 50.

Figure 7:
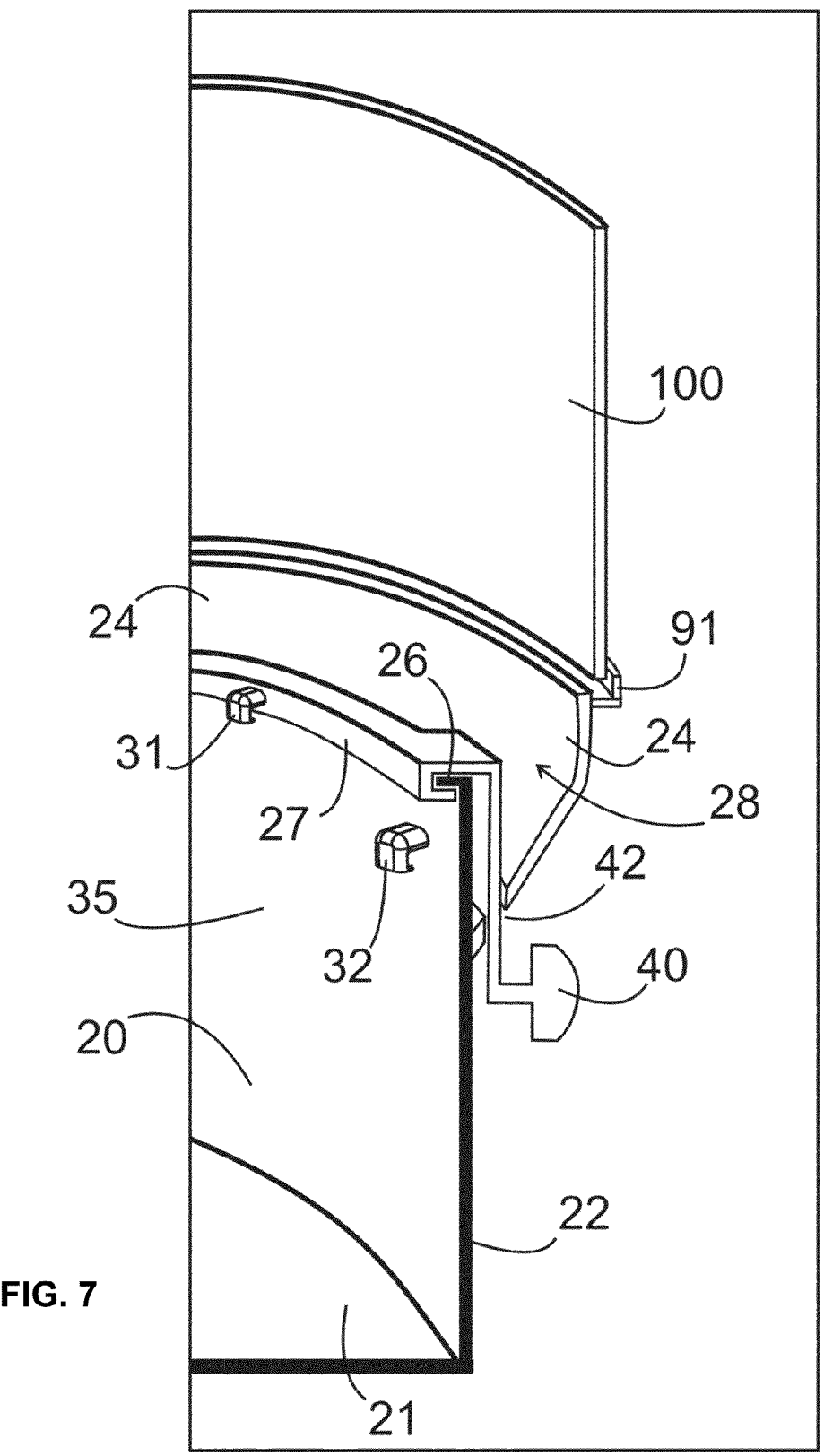
FIG. 7 is a cross sectional elevation view of the pet litter box showing the pan, the lid and the handle assembly.

As shown in FIG. 7, the L-shaped inner brim 26 engages with the C-shaped portion 27 of the main clutch 50. The C-shaped ring 27 then slides along the L-shaped ring 26.

On the backside of the C-shaped ring 27 facing the inner aspect of the pan 20, a plurality of downward facing hooks 31 is mounted at predefined distances from each other. A plurality of corresponding downward facing hooks 32 are also mounted on the upper portion of the internal wall 35 of the pan 20. The hooks 32 are attached in an elevation underneath the C-shaped ring 27 and are offset some length behind their corresponding upper hooks 31.

Figure 8A:
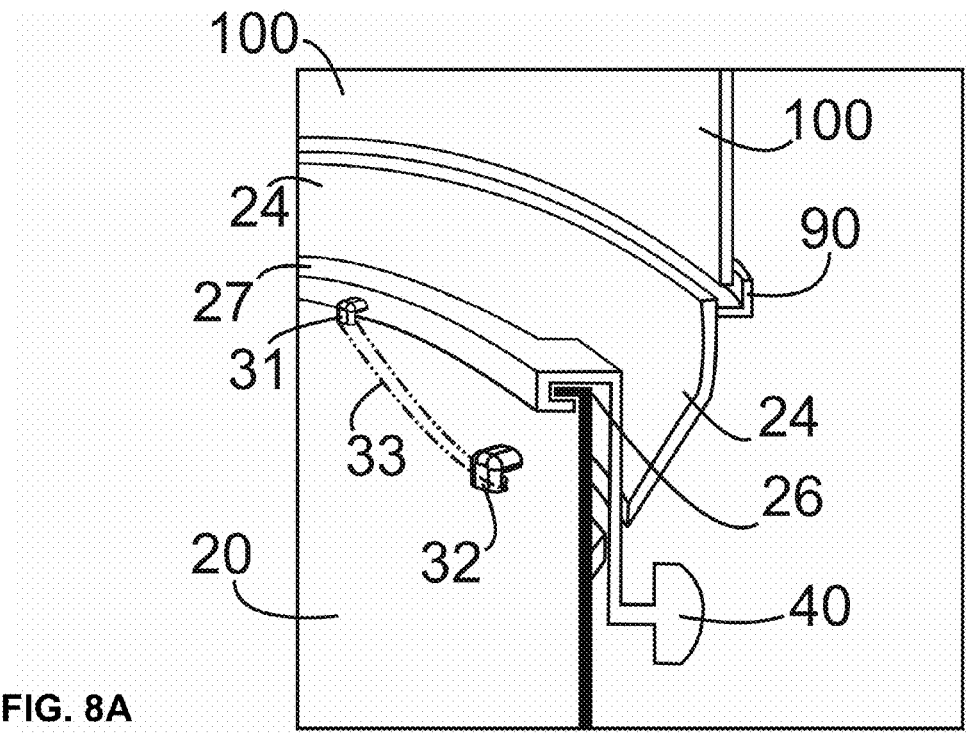
FIG. 8A is a fragmentary cross sectional view of the upper portion of the pan of the litter box, the handle and the position of the hooks and elastics mounted thereon.
Figure 8B:
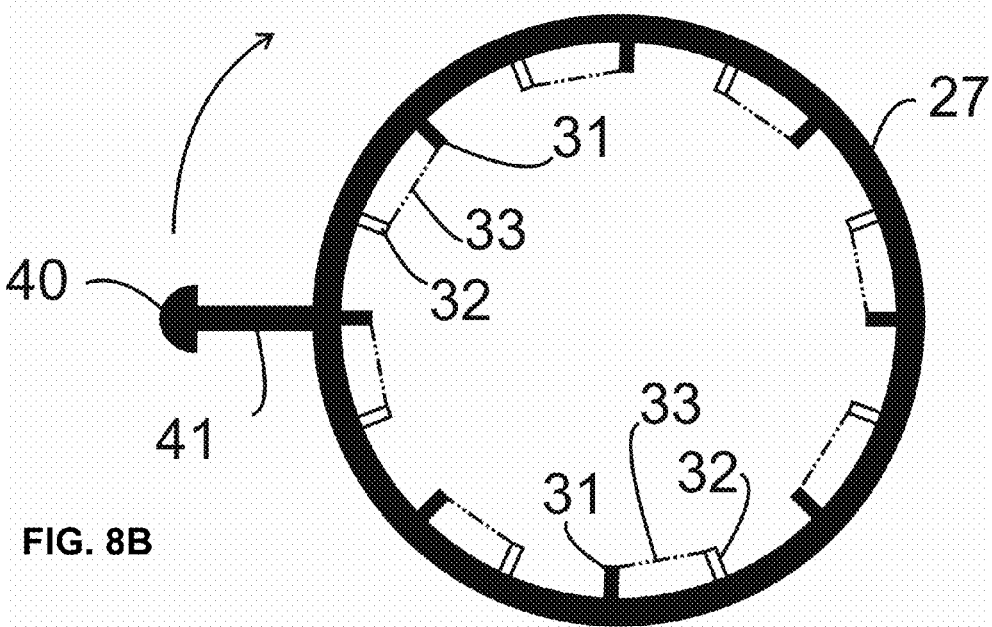
FIG. 8B is a top view of the upper portion of the pan, showing the main clutch system.

According to FIGS. 8A and 8B the hooks 31 and 32, in conjunction with a plurality of elastic bands 33, are part of the main clutch 50. Each of the upper hooks 31 support the leading end of the elastic band 33 attached to it and rotates around the circumference of the brim clockwise and away from its stationary corresponding hook 32. The clutch 50 further has a handle 40 with an arm 41 attached to the movable ring 27. The arm 41 moves through a peripheral slot allowing the movable ring 27 and the hooks 31 thereon to move and be operated from outside of the litter box.

Figure 9A:
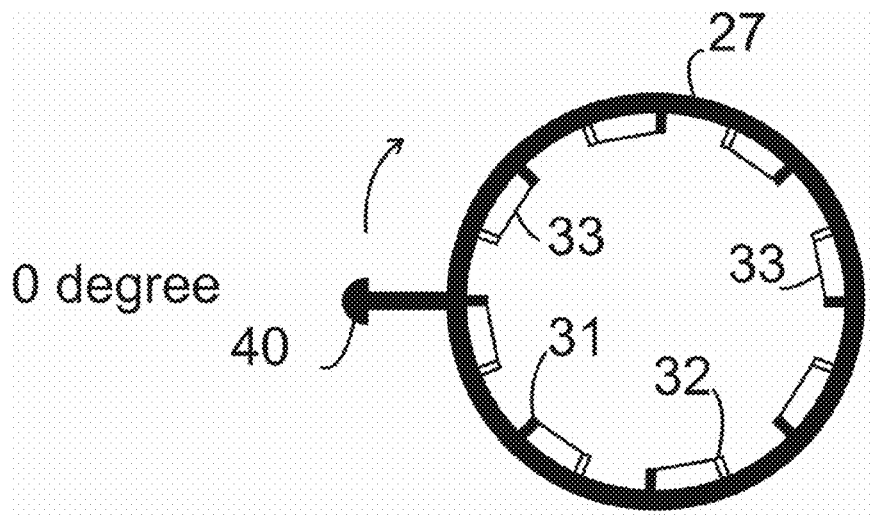
FIG. 9A is a top view of the upper portion of the pan, showing the steps of twisting system of the main clutch according to the present invention.
Figure 9B:
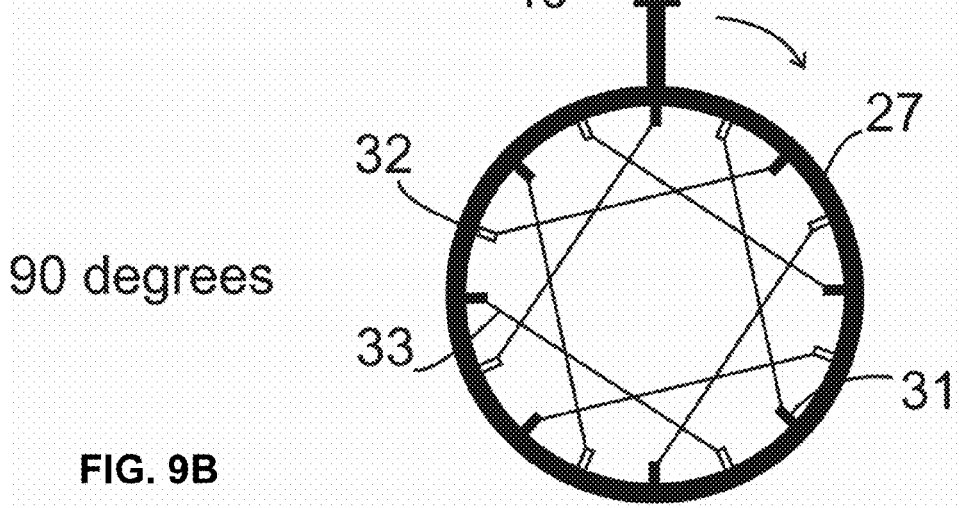
FIG. 9B is a top view of the upper portion of the pan, showing the steps of twisting system of the main clutch according to the present invention.
Figure 9C:
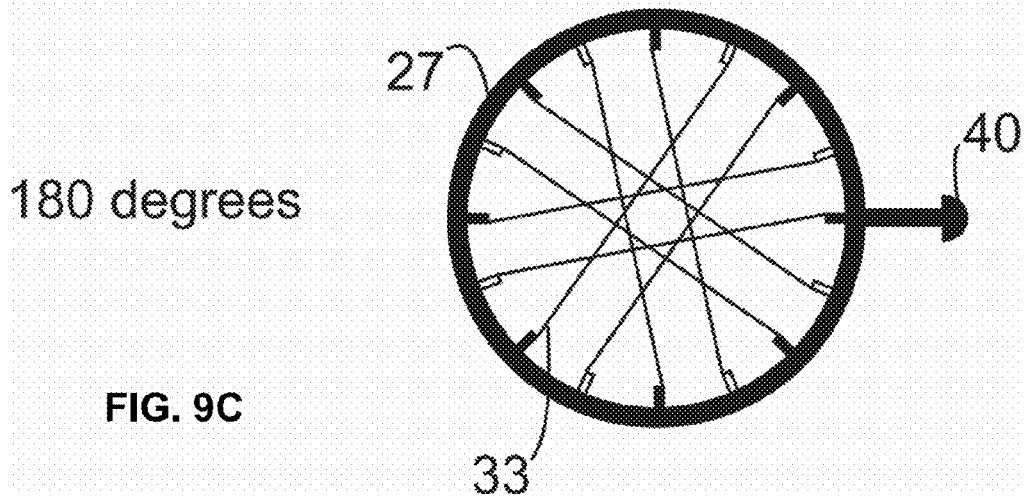
FIG. 9C is a top view of the upper portion of the pan, showing the steps of twisting system of the main clutch according to the present invention.

FIGS. 9A, 9B and 9C show how the moveable ring 27 of the clutch system in conjunction with the hooks 31, 32 and elastics 33 work to twist the litter bag. When the handle 40 moves clockwise, the movable ring 27, its hooks 31 and the ends of the elastic bands 33 attached to those hooks 31 rotate away from their corresponding stationary hooks 32, until finally coming to rest opposite of their starting point. These outstretched bands 33 become twisted above the centre of the pan, thereby twisting any bag set in the pan prior to activating the clutch.

Figure 10A:
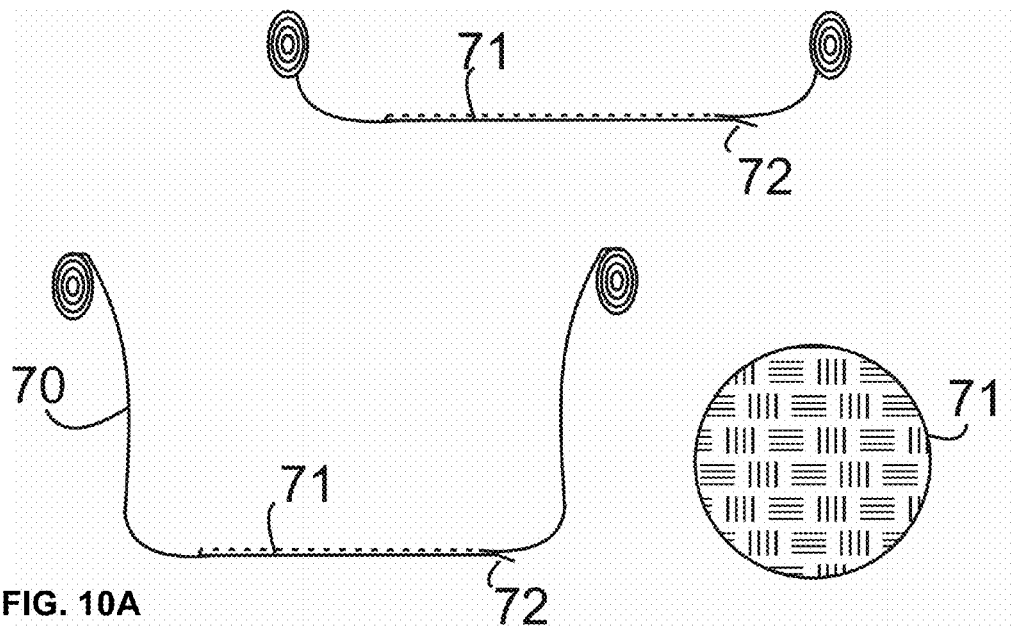
FIG. 10A shows the litter bag with perforated bottom according to the present invention.

FIG. 10A shows the litter bag 70 of the present invention. The bag 70 minimizes contamination of the pan 20 and conveniently collects waste for easy disposal, while preventing mess and unpleasant pan cleanups. Bags 70 preferably have a diameter of 24 inches and a length of 24 inches. During manufacturing, the length will be either rolled, like a condom or folded, like an accordion but retain a length of 5 inches or so to cover the sidewall of the pan and wrap over the inner brim and clutch. The perforated bottom of the bag 71 allows sifting for those wishing to separate waste from reusable litter once the exterior seal 72 is removed. A release tab is provided on the seal for easy removal of the seal by pulling on the tab. Seal 72 is reusable and can be used to seal the bag after the completion of the sifting to prevent content spillage during bag transportation.

Figure 10B:
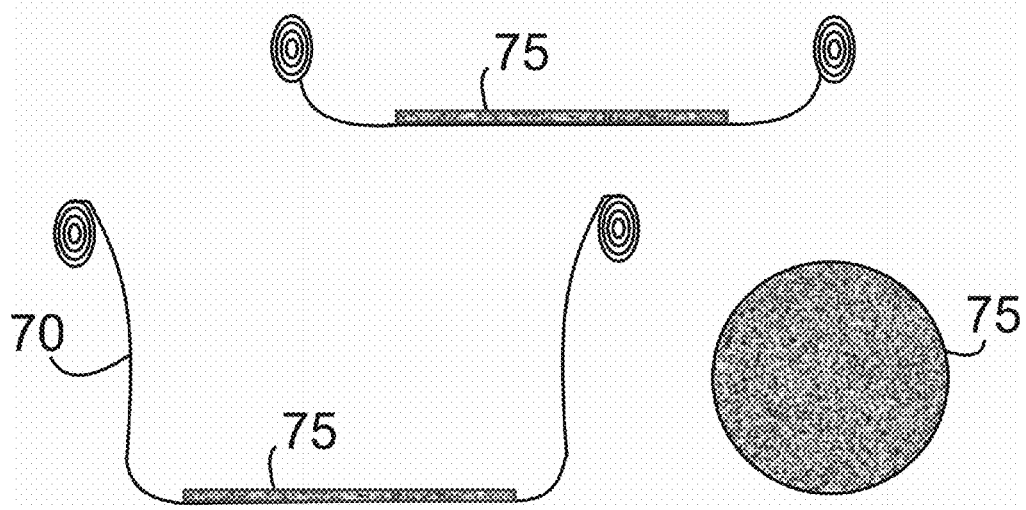
FIG. 10B shows the litter bag with absorbing pad bottom according to the present invention.

In another embodiment of the present invention as shown in FIG. 10B, an absorbing pad 75 is placed at the bottom portion of the litter bag 70. By having absorbing pad 75 at the bottom portion of the litter bag 70, small dogs can use the litter box.

FIGS. 11A and 11B show the litter bag 70 fitted in the litter pan 20. The bag-space 28 between the two brims 24 and 26, stores the rolled/corrugated portion of bag, keeping the litter box aesthetically pleasing and safe for the pets and securing the bag in the pan, while ensuring unhindered movement of the clutch.

The present invention preferably utilizes appropriate gauge scratch resistant bags made of biodegradable material, which can be made to attract cats and with rolled or corrugated top. Rolled/corrugated opening allows bag to be hidden neatly beneath lid, while affording sufficient slack for twisting.

In operation, a litter bag 70 is placed inside the pan 20 and the rolled edges are folded over the inner brim of the pan 26 and nestled in the cavity 28 created between the inner 26 and outer 24 brims of the litter pan 20. Litter is then added and the lid 100 is slid over the outer brim 24.

Figure 12:
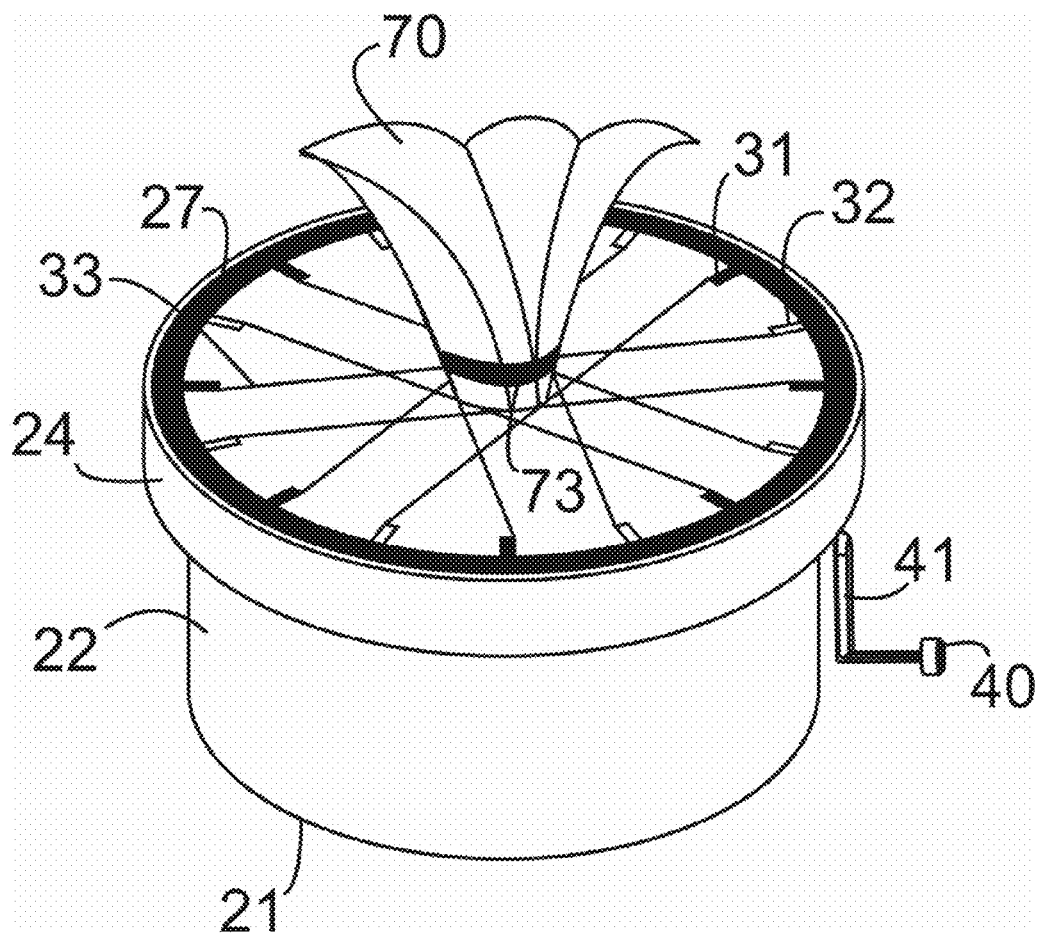
FIG. 12 is a perspective view of the litter pan in closed position showing the litter bag twisted closed inside the pan ready to be removed from the pan.

According to FIG. 12, the main clutch twists the litter bag 70, the excess bag material serves as slack to be unrolled, pulling the bag's edge toward the centre and twisting it. The combination of the bag's rolled top and bag space allows sufficient slack to be available, while eliminating the untidy fold over. This design also eliminates the need for the lid to rest on the bag, potentially interfering with the clutch's ability to gather it. The twisted litter bag 70 is then tied using any type of clip, like plastic clips 73 or can be knotted.

Figure 13:
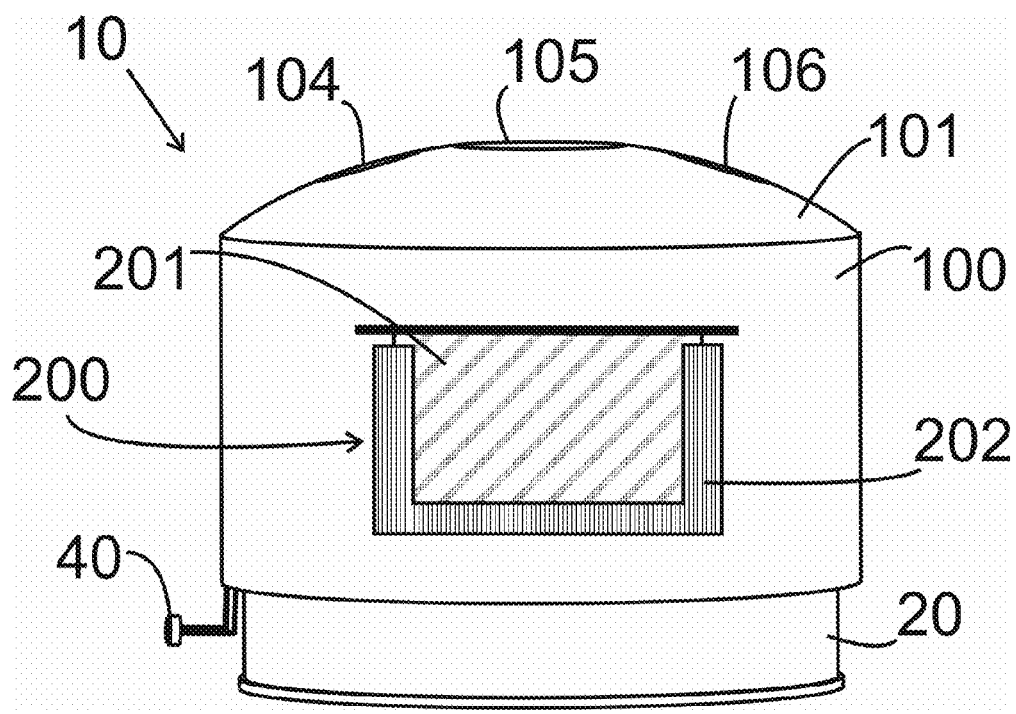
FIG. 13 is a perspective view of the litter box lid.

Referring to FIG. 13 the litter box lid 100 is shown, which is sized to be received on the litter pan 20, and comprises a top wall 101, cylindrical side wall and an open bottom portion. The lid top wall 101 defines a generally planar or curved surface. The lid 100 eliminates litter spatter and prevents bigger dogs from eating litter when used as a cat waste receptacle. In conjunction with the door 200, it also controls the escape of odours, dust, bacteria and noxious inhalants. The litter box lid 100 has a height sufficient to fit a large pet in it.

Figures 14A, 14B:
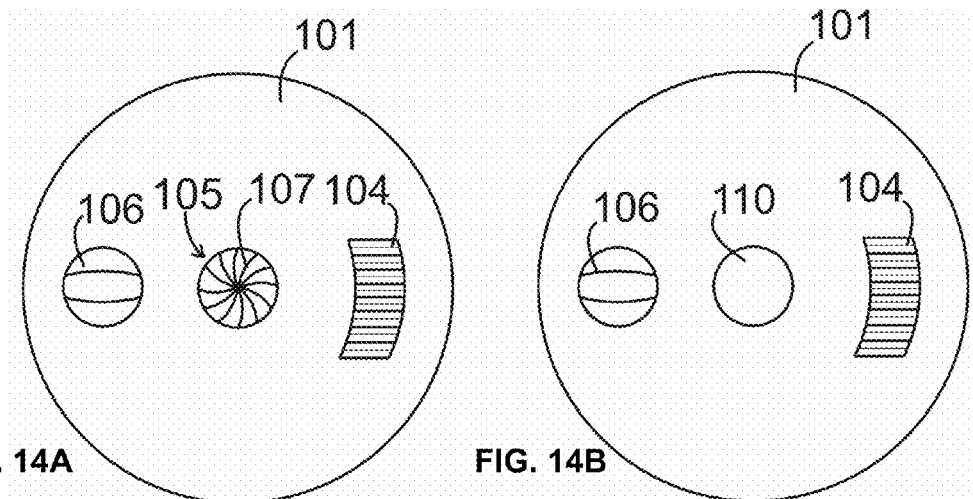
FIG. 14A is a top view of the top wall of the litter box lid showing the lid clutch according to an embodiment of the present invention.
FIG. 14B is a top view of the top wall of the litter box lid showing the lid window according to an embodiment of the present invention.

FIGS. 14A and 14B show one embodiment of the present invention, in which the lid top wall 101 of the litter box is equipped with a lid clutch 105 and a translucent lid window 110. These components 105 and 110 are interchangeable and sit in either the storage compartment 106 or the lid receptacle cavity, which is centered in the middle of the lid top wall 101. The top wall 101 also has a vent 104 to house a filtration system.

Figure 14C:
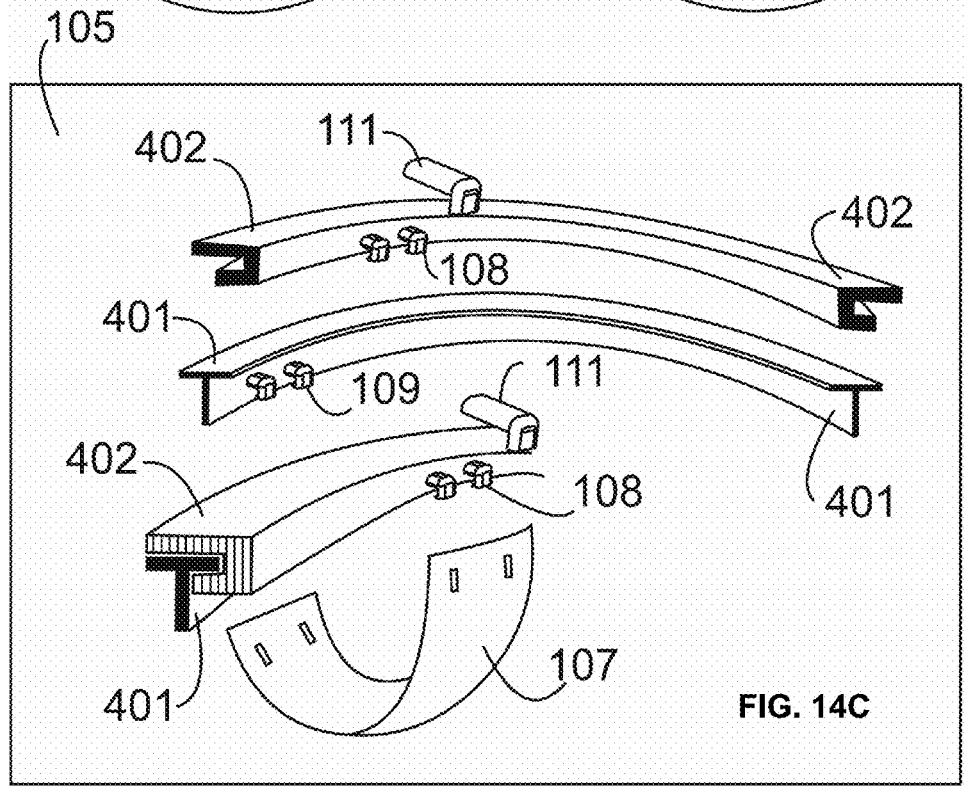
FIG. 14C is an explosion diagram of the lid clutch according to an embodiment of the present invention.

FIG. 14C is an explosion diagram of the lid clutch 105, as shown in an embodiment of this invention highlighted by FIGS. 14A and 14B. The lid clutch 105 is provided to hold the litter bag tight.

Figure 16A:
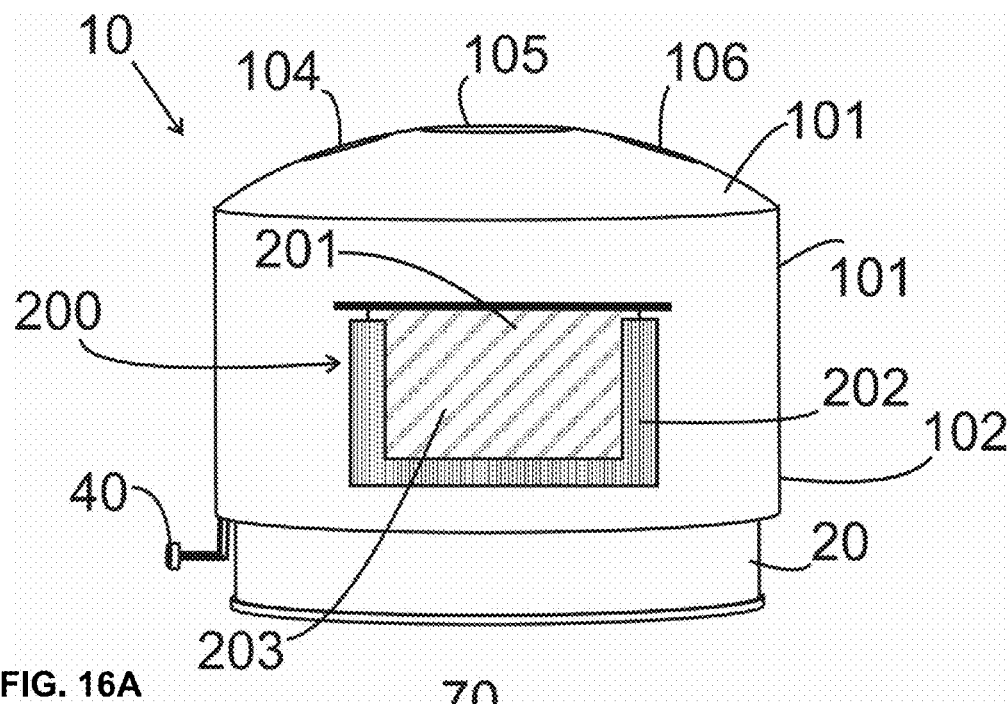
FIG. 16A is a perspective view of the litter box showing the overlapping electrostatic door.
Figure 16B:
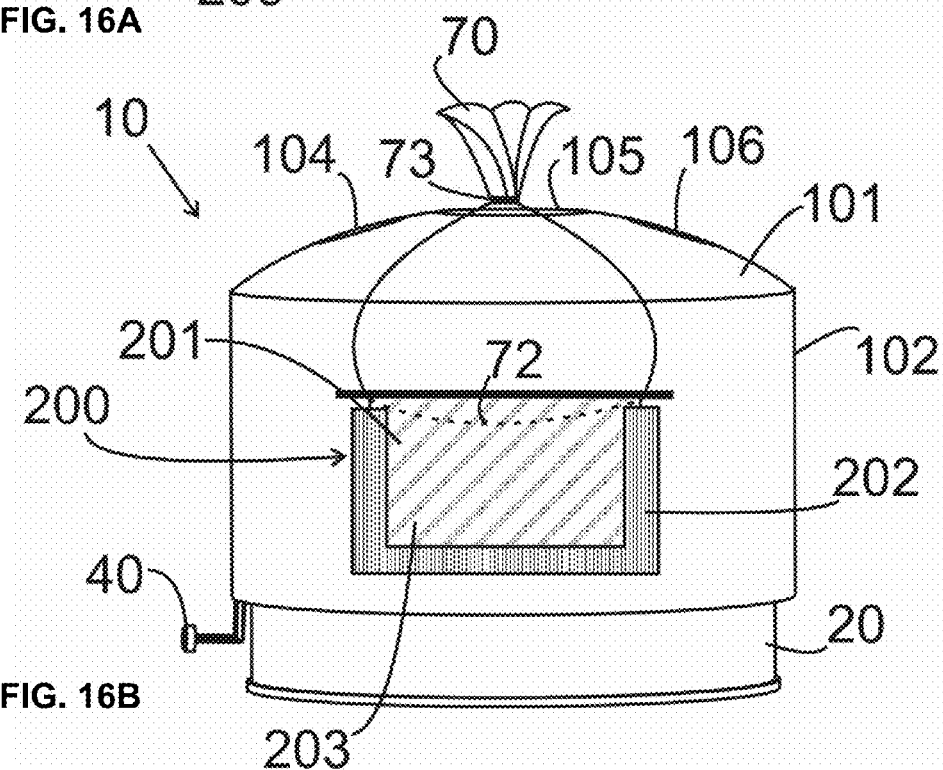
FIG. 16B is a view of the litter box of the present invention during use showing the litter bag clutched and ready to be sifted before disposal.

As shown in FIG. 16B the bag 70 is held by its top while hanging inside the litter box 10 for sifting purposes.

Again referring to FIG. 14C two concentric rings 401 and 402, are rotatably coupled to one another. The stationary ring 401 is shaped like a T and the outer ring 402 is shaped like a C, to allow for their rotational engagement.

The outer flange of the T ring 401 sits on the recessed lip of the lid receptacle cavity. The opposite end projects into the receptacle cavity and is engulfed by the C shaped movable ring 402, the top portion of which extends the entire length of the top portion of the T ring 401. The body of the T ring 401 falls into the space beneath the lid and it's inside circumference supports a plurality pairs of hooks, 109.

Again, referring to FIG. 14C on the back side of the C ring 402, are a plurality of hooks 108 that correspond to the hooks 109 on the stationary T ring. Like the main clutch, these hooks will be set forward on their C ring, when compared to the positioning of their corresponding hooks on the T ring. A plurality of appropriate material preferably Kevlar 107 is used to connect hooks on the T ring to the hooks on the C ring.

In open position, the Kevlar swatches 107 fall into the space beneath the lid forming a U shape, as two corners are affixed to the stationary ring 401 by hooks 109 and the other two are attached to the higher movable ring 402 via hooks 108. The lid clutch further has a handle 111. When the handle 111 is turned clockwise, the upper ring 402 moves taking with it one end of the Kevlar swatches 107. When the upper hooks 108 come to a stop at 180 degrees opposite their starting point, the lid clutch 105 is closed and the Kevlar swatches 107 are outstretched and intertwined such that they create a sealed barrier, tightly securing the litter bag 70 at an elevation from the litter pan base.

Figure 15A:
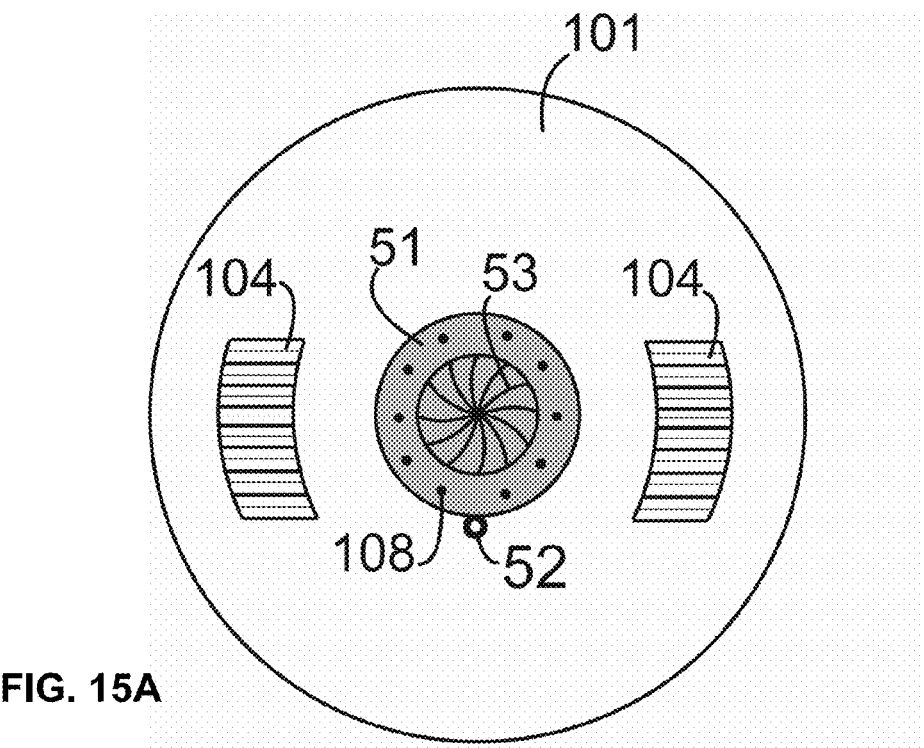
FIG. 15A is a top view of the top wall of the litter box lid showing the iris lid clutch according to another embodiment of the present invention.
Figure 15B:
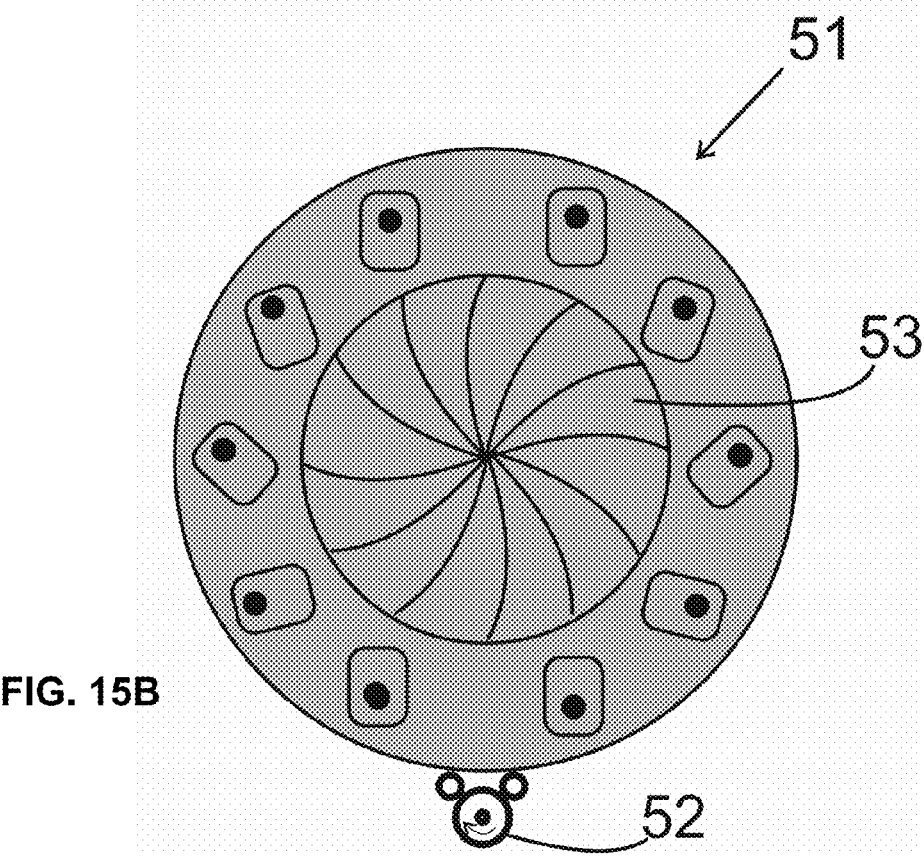
FIG. 15B is a schematic view of the iris lid clutch according to an embodiment of the present invention.

FIGS. 15A and 15B show another embodiment of the present invention wherein the lid clutch is a mechanical iris 51, which is surrounded by an internal ambient LED and UV-C LED lighting system (not shown). The clutch is constructed of a clear plastic so that it also functions as a window. FIG. 15B shows a possible construction for the mechanical iris 51, wherein a series of gears 53 are operated by the control knob 52. Regardless of the nature and construction of the blades or gears 53, they interact similarly with the control knob 52 and when open, the blades are tucked away within a circular compartment on the inner aspect of the lid top wall 101. This same compartment houses the gears and LED lights.

By turning the control knob 52 the operator can open and close the iris clutch 51 and by depressing it, can turn on or off the LEDs.

According to FIGS. 16A and 16B the litter box 10 further comprises an overlapping electrostatic or magnetic door 200 mounted on the door opening 203 cut into the front of the side wall 102 of the litter box lid, through which the pet enters and leaves the litter box 10. The door opening can be of any size, but preferably is 10 inches in height and 10 inches in width, and is covered by a swinging, removable door 200. Overlapping electrostatic or magnetic door 200 creates a tight seal to contain odors, dust, germs and toxic inhalants but swings effortlessly for easy ingress and egress by a pet. In an embodiment of the present invention the door has sensors to control the LED lights installed inside the lid top wall.

The door 200 can be slid down and snapped into place above the door opening 203 and can be removed as desired for those pets needing time to adjust to a covered bin. The litter box door 200 of the present invention provides a completely sealed system to prevent any odors from escaping from the litter box 10.

The door 200 comprises of two parts. A solid translucent plastic 201, which has a shape consistent with the curvature of the lid where it resides and a soft flexible plastic trim 202. The shape of the solid plastic component is that of a T with the vertical portion being substantially thicker than the letter it resembles. The soft flexible plastic trim 202 resembles that of a boxed U, that when fitted into the T component it is wider and longer than the former.

The top of door 201, which is solid, extends the full width of door opening 203 (e.g., 10 inches) and its length extends downward a height of ⅝ inches. It remains flush with the width of the door opening 203. At this measure the solid portion 201 becomes narrower (e.g., by one inch on each side leaving a total width of 8 inches with a remaining length of the door being 8⅜ inches). In position, the door leaves a 1 inch gap at the bottom of the door opening 203 and on both sides. The trim 202 is affixed to the edges of the door 200 and covers the entire 1 inch gap left by the solid door 201 and in fact extends beyond the gap to overlap the door opening 203 by ⅜ inches or an appropriate functional measure. The trim 202 is not attached to the sides of the door that are flush with the door opening 203.

The composition of the soft plastic trim 202 is such that it becomes highly electrostatic after coming into contact with a cat's fur. The continuous contact of the fur and plastic will provide a constant charge to the plastic, allowing it to cling via static electricity to the lid surrounding the door opening 203. It is this relationship that allows the door 200 to sit flush to the lid wall 102 and creates a barrier.

A cloth of appropriate material can also be used to manually rub along the trim to ensure that sufficient static electricity is available for the door to properly function when the box is used for small cats or kittens.

The measurements and materials of the aspects of the door 200 are determined such that the door swings easily to permit a small pet to enter and exit the litter box effortlessly. Therefore, the flexible plastic does not present an obstruction to the movement of the door and allows the door to consistently lie flat against the lid's inner and outer sides.

Figure 17:
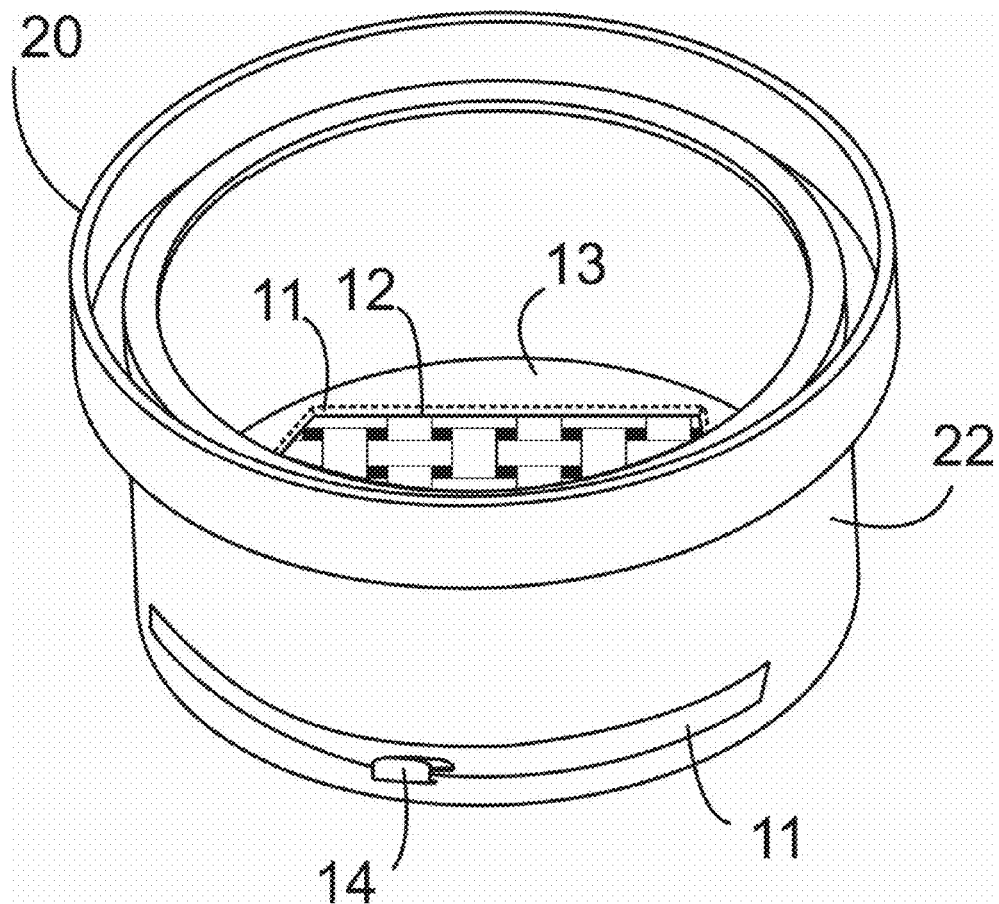
FIG. 17 is a perspective view of the inner part of the litter pan showing the tray and the litter mat according to the present invention.

As shown in FIG. 17, a removable litter mat 12 is provided inside a removable, retractable tray 11 in the litter pan 20. The mat 12 is sized to fit within the maximum dimensions of the inner surface of the litter pan 20. It can be of any material but specifically one that collects litter spatter and combs debris off of paws. In one embodiment, the mat 12 is nested inside a removable retractable tray 11 that is about fourteen inches square. The tray 11 has a handle 14 to allow it to slide in and out of the receiving cavity 13 built into the base of the pan 20 and has appropriate attachments that allow it to be removed and replaced easily.

Again according to FIGS. 14A, 14B and 15A, the litter box 10 further comprises of roof vent(s) 104 mounted on the top wall 101 of the lid. Said vent(s) 104 supports filters that filter contaminated air before it exits the lid 100. A variety of antimicrobial filters such as potassium infused activated carbon/zeolite or scented HEPA filters are slid into the vent(s) 104 and can be changed whenever are contaminated.

The present invention can be used in various ways. In one embodiment, the litter box 10 is used to achieve its intended purpose of hiding litter, controlling litter spatter and dust, and virtually eliminating the spread of odour, bacteria and noxious inhalants. For operators who prefer discarding the litter to sifting, they can use the lid window 110 (as shown in FIG. 14B) or the clutch window 51 (as shown in FIG. 15A) housed within the lid top 101 for periodic yet deliberate content inspection to determine when a change is needed. Once a change is necessary and with the pet outside of the litter box 10 and the door 200 facing the operator, the operator simply slides the handle 40 of the main clutch clockwise, (as shown in FIGS. 9A, 9B and 9C) from its open state at the 3 o'clock position, until it rests at its closed state at the 9 o'clock position. This action engages the elastic bands 33 attached to the upper ring 27 allowing them to spin and twist the bag 70. The lid 100 can be removed by lifting straight up at any time after the clutch is closed. However, given the foul odours lingering beneath the lid, it is preferred to allow the air to circulate via the roof vent 104 before removing the lid 100.

Once the lid 100 is removed, the bag 70 is permanently closed by applying a bag clip 73 or knotting the bag. After the clip is applied, the clutch 50 is returned to the neutral position, releasing the bag 70 so that it can be lifted out of the pan 20 and disposed.

A new bag 70 is then placed into the pan 20 and secured by folding it over the inner brim 26 and nestling it into the brim cavity 28. Any debris caught in the litter mat 12 is returned to the pan 20 by removing the litter mat 12 and turning it upside down over the pan 20. Finally, the mat 12 is reapplied and clean litter is added to the pan 20 and the lid 100 is placed back on the pan.

Again referring to FIG. 16B, in operation, when the operator intends to separate waste from reusable litter, the combination of the door 200, lid clutch 105 and lid 100 creates a sealed system that controls the aerosolization of dust, bacteria, noxious inhalants and odour into the surrounding environment. In this case, rather than disposing the used bag 70, after it is clipped and lifted out of the pan, a new bag 70 is secured in the pan 20 and then the used bag is set back in the pan. The bag should be set such that the release tab of the reusable seal 72 is located opposite to the mat's center point or in the 12 o'clock position. The lid 100 is then put back. In an embodiment of this invention, the lid clutch 105 is removed from the clutch storage compartment 106 and exchanged with the lid window 110. The lid clutch 105 is then opened, so that the operator can reach into the litter box 10 and pull up the used bag 70, ensuring that a sufficient amount of bag projects through the receptacle to allow the bag's bottom to become suspended at a reasonable elevation above the pan 20, while taking care not to change the bag's orientation in the litter box.

The lid clutch 105 is then closed, causing the Kevlar swatches 107 to twist, sealing the opening and tightly holding the bag suspended inside the box.

The operator can then reach into the litter box 10 via the door 200 and pull the bag's release tab, removing the reusable seal 72 and setting it with its outer side on the floor. The sifting process occurs through the perforations at the bottom of the bag. Once the sifting process is completed, the operator can take a hold of the top of the used bag, open the clutch 105 and set the used bag 70 back down in the pan and then close the clutch 105. Given that the aerosolized particles may be lingering inside the box 100, it is preferred that some time is allowed for the air to circulate via the roof vent 104 before opening the lid clutch 105.

Once the bag 70 is set back in the litter pan 20 and the lid clutch 105 is closed, the lid clutch 105 is swapped with the lid window 110. The lid 100 is removed and the used bag 70 is taken out of the pan 20 and set back on the reusable seal 72, so as to cover the perforations 71 and allow the bag to be disposed without the risk of content spillage. Clean litter is then added to the pan as needed, the mat is emptied and the lid is put back on as described earlier.

The system can also be used without a lid. This may be necessary for larger pets or due to limitations in space, etc. In such cases, the pan with just the bag is used. The main clutch assembly provides a good control over the litter spatter. In this application, the operator can utilize the clutch to close the bag and then choose whether to simply toss a full bag, hold the bag or apply the lid for sifting or scoop.

In another embodiment of the present invention, the lid is further provided with internal ambient LED lighting and a UV-C LED disinfection system. The microorganisms from pets' litter can spread to the space outside of the pan. For this reason and to minimize contamination, the lid interior is coated with a reflective material to enhance the effect of both the ambient and UV-C LEDs. The disinfection system is activated only when the door closes and the ambient LEDs turn off once the pet has left the bin. The UV-C system is set to operate for a defined length of time to disinfect the air and litter, killing up to 99.99% of microorganisms beneath the lid. The UV-C system is set to immediately deactivate if the door swings inward during its operation, while simultaneously activating the ambient LED lights. UV-C light destroys the nucleic acids of microorganisms disrupting their DNA, leaving them unable to perform vital cellular functions like reproduction. Wave lengths of 100-300 nm and doses between 2-8 mJ/cm2 are effective ranges for germicidal irradiation. Wave lengths of 265 nm produce peak effects and a dose of 21.6 mJ/cm$^2$ will kill 99.99% of microorganisms. The ambient LEDs and UV-C LEDs are the preferred system for the present invention, however other options, such as a bulb can be used for ambient and UV lighting.

The ambient LEDs and UV-C LEDs are housed within the top wall of the lid that encloses the gears and blades for the iris clutch. They can be installed in alternate and in a ring fashion. The LEDs are powered by a rechargeable lithium ion battery housed within the control knob on the lid. They are connected to two switches, one operated by the door and the other by depressing the control knob. The beginning of a cycle is when all LEDs are off and the door lies adjacent to the exterior of the lid.

As the door swings inward to allow the pet to enter, the ambient LEDs are turned on to illuminate the interior and make use easier. They will remain on for 5 minutes or until the door swings outward and comes to rest on the exterior lid wall after the pet exits, whichever is shorter.

Once the door rests on the external lid wall, the ambient LEDs turn off and a 30 second timer commences, at the end of which time, the UV-C LEDs are turned on and run for an appropriate length of time to effect disinfection. The UV-C timer will only begin if the door is elevated above 45 degrees, to ensure no accidental opening by the pet inside the litter box triggers the system to start.

After the disinfection period is complete or should the door swing inwards again during disinfection, the UV-C LEDs is immediately turned off and in the latter case, the ambient LEDs are turned on. In either event, the cycle is at its starting point.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A pet litter box to collect pet wastes comprising of:
   a. a cylindrical litter pan having a pan-diameter, a center, an outer wall, an inner wall and an open top end comprising of:
      i. an inner brim at said open top end having an inner-brim diameter, said inner brim extending radially inward toward said center;
      ii. an outer brim having an outer-brim diameter and connected to said outer wall, wherein said outer-brim diameter is larger than said inner-brim diameter forming a bag-space between said inner and outer brims;
      iii. a semi-circular groove constructed in said outer brim;
      iv. a movable circular ring having means to rotatably engage to said inner brim;
      v. a handle attached to said movable circular ring, said handle extending out of said outer brim from said semi-circular groove;
      vi. a plurality of stationary pan-hooks installed at a top portion of said inner wall and at a predefined space from each other;
      vii. a plurality of movable ring-hooks installed at said inner side at a predefined space from each other; and
      viii. a plurality of elastic bands, each band attaching a pair of adjacent pan-hooks and ring hooks;
   b. a litter lid to be placed on said litter pan and having a lid-top and an opening to allow a pet to enter and exit said litter box; and
   c. a litter bag having an open end and a closed end, wherein said closed end is set inside said litter pan and said open end is rolled and stored in said bag-space, whereby by turning said handle, said elastic bands twist said litter bag and close said open end.

2. The pet litter box of claim 1, wherein said litter bag having a perforated portion with a removable seal at said closed end, wherein said bag is used for sifting the litter.

3. The pet litter box of claim 1, wherein said litter bag having an absorbing pad at said closed end.

4. The pet litter box of claim 1, wherein said means to rotatably engage to said inner brim is a C-shaped slot sized to be engaged with said inner brim.

5. The pet litter box of claim 1, wherein said cylindrical litter pan preferably having 4.5 inches height and 24 inches in diameter.

6. The pet litter box of claim 1, wherein said litter pan further has a hollowed cavity to receive a removable and retractable tray, wherein said tray sized to receive a mat.

7. The pet litter box of claim 1, wherein said litter bag preferably having a 24 inches diameter and 24 inches length.

8. The pet litter box of claim 1, wherein said litter lid further having a grabbing means to grab and hold said litter bag for sifting.

9. The pet litter box of claim 8, wherein said grabbing means comprising of a first ring, a second ring, a plurality of hooks on said first and second rings, a plurality of bands connecting said hooks, and a clutch that rotates one ring with respect to other ring thereby grabbing and holding said litter bag.

10. The pet litter box of claim 8, wherein said grabbing means is comprised of a transparent mechanical iris and control knob to open and close a plurality of blades, wherein said blades grab and hold said litter bag.

11. The pet litter box of claim 1, wherein said lid-top further having a roof vent to allow air circulation inside said pet litter container.

12. The pet litter box of claim 11, wherein said roof vent further having an air filtration system.

13. The pet litter box of claim 1, wherein said litter lid further having a reflective interior coating, ambient LEDs and a UV-C LED disinfection system to illuminate litter box interior and prevent spread of the microorganisms from pet litter.

14. The pet litter box of claim 1, wherein said pet litter box further having a control knob to activate said LEDs.

15. The pet litter box of claim 1, wherein said litter bag is made of a biodegradable material and is infused with a material that attracts pets.

16. The pet litter box of claim 1, wherein said pet litter box is made of a non-stick antimicrobial plastic.

17. The pet litter box of claim 1, wherein said door comprises of a first section that is smaller than said opening and a second section attached to said first section and overlapping the body of said litter lid, wherein said second section is made of a soft flexible plastic which becomes highly electrostatic by coming into contact with a pet's fur, thereby clinging to said litter lid.

18. The pet litter box of claim 17, wherein said first section is made of a solid translucent plastic.

19. A box to collect wastes comprising of:
   a. a cylindrical pan having a pan-diameter, a center, an outer wall, an inner wall and an open top end comprising of:
      i. an inner brim at said open top end having an inner-brim diameter, said inner brim extending radially inward toward said center;
      ii. an outer brim having an outer-brim diameter and connected to said outer wall, wherein said outer-brim diameter is larger than said inner-brim diameter forming a bag-space between said inner and outer brims;
      iii. a semi-circular groove constructed in said outer brim;
      iv. a movable circular ring having means to rotatably engage to said inner brim;
      v. a handle attached to said movable circular ring, said handle extending out of said outer brim from said semi-circular groove;
      vi. a plurality of stationary pan-hooks installed at a top portion of said inner wall and at a predefined space from each other;
      vii. a plurality of movable ring-hooks installed at said inner side at a predefined space from each other; and
      viii. a plurality of elastic bands, each band attaching a pair of adjacent pan-hooks and ring hooks; and
   b. a bag having an open end and a closed end, wherein said closed end is set inside said pan and said open end is rolled and stored in said bag-space,
   whereby by turning said handle, said elastic bands twist said bag and close said open end.

\* \* \* \* \*